US005538737A

United States Patent [19]

Leonard et al.

[11] Patent Number: 5,538,737
[45] Date of Patent: Jul. 23, 1996

[54] ORAL COMPOSITIONS OF $H_2$-ANTAGONISTS

[75] Inventors: Thomas W. Leonard; David P. Hause; Frederick D. Sancilio, all of Wilmington; James Swarbrick, Hampstead; Edward S. Wilson, Wilmington, all of N.C.

[73] Assignee: Applied Analytical Industries, Inc., Wilmington, N.C.

[21] Appl. No.: 347,586

[22] Filed: Nov. 30, 1994

[51] Int. Cl.[6] .................................................. A61K 9/48
[52] U.S. Cl. .................... 424/451; 424/455; 424/456; 514/938; 514/943
[58] Field of Search .................................. 424/451, 455, 424/456; 514/937

[56] References Cited

U.S. PATENT DOCUMENTS

| | | | |
|---|---|---|---|
| 3,376,199 | 4/1968 | James et al. | 167/83 |
| 4,128,658 | 12/1978 | Price et al. | 424/285 |
| 4,169,855 | 10/1979 | Price et al. | 260/583 |
| 4,279,819 | 7/1981 | Price et al. | 260/326.5 |
| 4,521,431 | 6/1985 | Crookes | 514/471 |
| 4,585,790 | 4/1986 | Padfield et al. | 514/471 |
| 4,672,133 | 6/1987 | Crookes | 549/495 |
| 4,711,782 | 12/1987 | Okada et al. | 424/455 |
| 4,880,636 | 11/1989 | Franz | 424/480 |
| 5,007,790 | 4/1991 | Shell | 424/451 |
| 5,028,432 | 7/1991 | Chopra et al. | 414/451 |
| 5,032,393 | 7/1991 | Douglas et al. | 424/79 |
| 5,068,249 | 11/1991 | Long | 514/471 |
| 5,102,665 | 4/1992 | Schaeffer | 424/466 |
| 5,169,855 | 10/1979 | Price et al. | 260/583 |
| 5,169,864 | 12/1992 | Johnson et al. | 514/471 |
| 5,175,147 | 12/1992 | Folkman et al. | 514/12 |
| 5,206,219 | 4/1993 | Desai | 514/3 |
| 5,229,137 | 7/1993 | Wolfe | 424/687 |
| 5,271,945 | 12/1993 | Yoshioka et al. | 424/489 |
| 5,304,571 | 4/1994 | Johnson et al. | 514/471 |
| 5,330,767 | 7/1994 | Yamamoto et al. | 424/497 |
| 5,348,748 | 9/1994 | Sheth et al. | 424/494 |
| 5,360,615 | 11/1994 | Yu et al. | 424/455 |

FOREIGN PATENT DOCUMENTS

| | | |
|---|---|---|
| 1565966 | 4/1980 | United Kingdom . |
| 2222772 | 3/1990 | United Kingdom . |
| WO94/08560 | 4/1991 | WIPO . |
| WO94/08576 | 4/1994 | WIPO . |

OTHER PUBLICATIONS

R. Teraoka et al., *Effects of Temperatures and Relative Humidity on the Solid–State Chemical Stability of Ranitidine Hydrochloride* American Pharmaceutical Association 82(6) pp. 601–604 (1993).

Chem. Abstracts 114:129112q *Ranitidine capsules* (1990).

Madan, et al., Preparation and Characterization of Ranitidine–HCl Crystals *Drug Development and Industrial Pharmacy* 20(9):1571 (1994).

Teraoka, et al., Effects of Temperature and Relative Humidity on the Solid–State Chemical Stability of Ranitidine Hydrochloride *Journal of Pharmaceutical Sciences* 82(6):601 (1993).

P. P. Constantinides, et al; *Formulation and Intestinal Absorption Enhancement Evaluation of Water–in –Oil Microemulsions Incorporating Medium–Chain Glycerides, Pharmaceutical Research* 11 No. 10, pp. 1385–1390 (1994).

Notification of Transmittal of the International Search Report or the Declaration; PCT/US95/15256.

*Primary Examiner*—Thurman K. Page
*Assistant Examiner*—James M. Spear
*Attorney, Agent, or Firm*—Bell, Seltzer, Park & Gibson

[57] ABSTRACT

The present invention provides pharmaceutical capsule compositions for the oral administration of an $H_2$-antagonist. The composition includes a capsule containing an emulsion having a water portion and an oil portion. A pharmaceutically acceptable salt of an $H_2$-antagonist is dissolved in the water portion. The composition delivers a therapeutically effective amount of the $H_2$-antagonist to a patient in need thereof. The present invention also provides methods of making the capsule composition.

47 Claims, No Drawings

ORAL COMPOSITIONS OF H₂-ANTAGONISTS

FIELD OF THE INVENTION

This invention relates to oral delivery systems for pharmaceutically active agents and more particularly to new oral pharmaceutical delivery products for $H_2$-antagonist agents.

BACKGROUND OF THE INVENTION

The $H_2$-antagonist agents (hereinafter "$H_2$-antagonists") are routinely administered orally to patients suffering from gastrointestinal conditions such as ulcers, dyspepsia, various reflux indications and the like. Typically, the $H_2$-antagonist is delivered to the patient in tablet or powder-filled capsule form. Other liquid oral compositions such as syrups have also been proposed (see, U.S. Pat. No. 4,128,658 to Price et al.)

The $H_2$-antagonists are known to have an unpalatably bitter taste when ingested in any form other than solid capsule or tablet form. Additionally, capsules or tablets, which contain the drug in solid crystalline form, may exhibit non-uniform absorption characteristics because of multiple polymorphic forms. Some $H_2$-antagonists exhibit multiple polymorphic forms, and absorption characteristics can vary between these forms. In addition, polymorphic forms may not be stable, and may undergo transformation in the solid dosage forms. Alternative formulations targeted at resolving these disadvantages have been proposed. For example, PCT WO94/08560 and U.S. Pat. No. 5,068,249 to Schaeffer propose chewable or effervescent tablets. U.S. Pat. No. 5,008,256 to Long proposes formation of complexes of $H_2$-antagonists. U.S. Pat. No. 5,032,393 to Douglas et al. proposes resin adsorption. PCT WO94/08576, and U.S. Pat. Nos. 5,028,432 to Chopra et al. and 5,007,790 to Shell propose non-aqueous formations of $H_2$-antagonists in fats or oils. U.S. Pat. No. 5,229,137 to Wolfe proposes solid or liquid formulations which include an $H_2$-antagonist in combination with an antacid.

One $H_2$-antagonist, ranitidine, also has been reported to be incorporated into a non-aqueous composition comprised of a solid wax or oil such as "Miglyol" and a surfactant such as lecithin, and then filled into a gelatin capsule. See, C.A. 114(14) 129112. U.S. Pat. No. 4,585,790 to Padfield et al. proposes oral and injectable aqueous compositions of ranitidine having a pH range from 6.5 to 7.5. However these solutions are known to exhibit stability problems for injectable administration or when the solids are exposed to hygroscopic conditions. See, R. Tenaoka et al. J. Pharm. Sci. 82, 601 (1993).

Other methods of administering various pharmaceuticals, including other anti-ulcer drugs have been proposed. For example, U.S. Pat. No. 4,711,782 to Okada et al. proposes a microcapsule containing a drug and a drug retaining substance, which is formed by preparing a water-in-oil emulsion, thickening or solidifying the aqueous layer, and subjecting the resulting emulsion to in-water drying to provide a solid formulation.

SUMMARY OF THE INVENTION

As a first aspect, the present invention provides a pharmaceutical capsule composition for the oral administration of a pharmaceutically active agent, e.g., an $H_2$-antagonist. The composition includes a capsule containing a water-in-oil emulsion having a water portion and an oil portion. A pharmaceutically acceptable salt of the pharmaceutically active agent is dissolved in the water portion. The water-in-oil emulsion is compatible with the capsule into which it is filled. The composition delivers a therapeutically effective amount of the agent to a patient in need thereof.

Advantageously, the product is not subject to the vagaries of polymorphism, because the pharmaceutically active agent is in solution. The pharmaceutically active agent being in solution allows for more rapid delivery of the compound, and obviates concerns about polymorphic instability and transformation. The salt of the pharmaceutically active agent is sufficiently soluble in the aqueous medium to avoid the formation of crystals of the pharmaceutically active agent. As a second advantage, the composition of the present invention provides a liquid composition (i.e., an emulsion) of the pharmaceutically active agent for oral administration while overcoming the unpalatably bitter taste of previously known liquid formulations. In addition, the liquid emulsion is advantageously compatible with the capsule walls. It is known in the art that aqueous solutions, e.g., water, and many hydrolytic solvents attack starch or gelatin capsules. However, the compositions of the present invention provide a liquid water-in-oil emulsion which does not degrade the walls of starch or gelatin capsules.

As a second aspect, the present invention provides a method of forming an emulsion containing an $H_2$-antagonist. The method includes (a) dissolving a pharmaceutically acceptable salt of an $H_2$-antagonist in an aqueous medium to form a water portion, (b) combining the water portion with an oil portion including an edible oil and an emulsifying agent to form a water portion and oil portion matrix, and (c) emulsifying the matrix to form the emulsion.

As a third aspect, the present invention provides an alternate method of forming an emulsion containing an $H_2$-antagonist. The method includes (a) dissolving a free base of an $H_2$-antagonist in an inorganic acid medium to form a water portion, (b) combining the water portion with an oil portion including an edible oil and an emulsifying agent to form a water portion and oil portion matrix, and (c) emulsifying the matrix to form the emulsion.

As a fourth aspect, the present invention provides a method of making a pharmaceutical capsule composition for the oral administration of a therapeutically effective amount of a pharmaceutically active agent, e.g. , an $H_2$-antagonist. The method includes (a) dissolving a pharmaceutically acceptable salt of the $H_2$-antagonist in an aqueous medium, (b) combining the water portion with an oil portion including an edible oil and an emulsifying agent, to form a water portion and oil portion matrix, (c) emulsifying the matrix to form the emulsion, and (d) filling the capsule with the emulsion. The edible oil of the oil portion of the emulsion is compatible with the capsule, such that the emulsion does not degrade the capsule wall.

As a fifth aspect, the present invention provides an alternate method of making a pharmaceutical capsule composition for the oral administration of a therapeutically effective amount of a pharmaceutically active agent, e.g., an $H_2$-antagonist. The method includes (a) dissolving a free base of the $H_2$-antagonist in an inorganic acid medium, (b) combining the water portion with an oil portion including an edible oil and an emulsifying agent, to form a water portion and oil portion matrix, (c) emulsifying the matrix to form the emulsion, and (d) filling the capsule with the emulsion.

The foregoing and other aspects of the present invention are explained in detail in the specification set forth below.

DETAILED DESCRIPTION OF THE INVENTION

The term "emulsion" as used herein refers to a uniform, liquid or semisolid dispersion of immiscible liquids. As used herein, the term "semisolid" refers to an emulsion having a consistency ranging from that of a lotion to that of a thick cream. The emulsions of the present invention are distinguishable from pharmaceutical suspensions which include a solid form dispersed in a liquid medium. The emulsions of the present invention are comprised of a water portion and an oil portion, and may be in the form of a water-in-oil emulsion, wherein the water is the dispersed phase and the oil is the continuous phase, or an oil-in-water emulsion, wherein the oil is the dispersed phase and the water is the continuous phase. In addition, the emulsions of the present invention may be in the form of a "microemulsion," meaning that the emulsion is in a form of continuous and dispersed phases wherein the droplet size is sufficiently small that the emulsion appears transparent. Microemulsions may also consist of essentially stable, single-phase swollen micellar solutions. The term "dissolved" as used herein means that the pharmaceutically active agent is sufficiently soluble in, and solubilized in the water portion of the emulsion such that no crystal formation, as measured by X-ray crystallography, occurs.

According to the present invention, pharmaceutical capsule compositions are prepared. The compositions are suitable for the oral administration of a variety of pharmaceutically active agents. According to one embodiment, the compositions are prepared by (a) dissolving a pharmaceutically acceptable salt of the pharmaceutically active agent in an aqueous medium to form a water portion, (b) combining the water portion with an oil portion to form a water portion and oil portion matrix, (c) emulsifying the matrix, and (d) filling a capsule with the thus prepared emulsion. According to a second embodiment, the capsules are prepared by (a) dissolving a free base of the pharmaceutically active agent in an inorganic acid medium to form a water portion, (b) combining the water portion with an oil portion to form a water portion and oil portion matrix, (c) emulsifying the matrix, and (d) filling a capsule with the thus prepared emulsion.

As noted above, the compositions may be prepared with a variety of pharmaceutically active agents including $H_2$-antagonists, $H_1$-antagonists, anti-inflammatory agents, tranquilizers, cardiotonic agents, anti-bacterial agents, anti-depressant agents, anti-obesity agents, anti-hyperglycemic agents, anti-emetic agents, corticosteriods, gastric motility enhancing agents and renal function improving agents. Compositions prepared with $H_2$-antagonists are currently preferred. Compounds which have $H_2$-antagonist activity (i.e., $H_2$-antagonists) are used to treat various gastrointestinal disorders such as ulcers, dyspepsia or reflux indications.

$H_2$-antagonists are derivatives of histamine that stereospecifically bind to and exhibit inhibiting or blocking activity against $H_2$ receptors. The $H_2$-antagonists, or "$H_2$-blocking agents," are a discrete and limited group of medications readily recognized in the art, and are generally polar, hydrophobic molecules. See, Goodman and Gilman's *The Pharmacological Basis of Therapeutics*, 7th ed. pp 624–625 (1985). Examples of $H_2$-antagonists include but are not limited to ranitidine, cimetidine, nizatidine, famotidine, sufotidine, roxatidine, bisfentidine, tiotidine, lamtidine, niperotidine, mifentidine, zaltidine, and loxtidine. $H_2$-antagonists that are imidazole derivatives (e.g., cimetidine) and furan derivatives (e.g., ranitidine) are preferred. Ranitidine is currently most preferred.

The pharmaceutically active agents useful in the present invention are preferably provided in the form of a pharmaceutically acceptable salt or a free base. Suitable salts are readily available and well known in the art. The preferred pharmaceutically acceptable salts are water soluble. The $H_2$-antagonists may be provided in a variety of water-soluble salt forms. Suitable water soluble salt forms include hydrochloride salts, hydrobromide salts, hydroiodide salts, hydrofluoride salts, sulfate salts, nitrate salts, citrate salts and tartrate salts. The hydrochloride salts are currently preferred.

The water portion, into which the salt form of the pharmaceutically active agent is dissolved comprises an aqueous medium. As used herein, the term "aqueous medium" refers to a liquid consisting primarily of water, normally greater than about 90 percent water, and which can be essentially pure water in certain circumstances. For example, an aqueous medium can be distilled water, tap water, or the like. Typically, the aqueous medium is water. However, those skilled in the art will appreciate that other additives such as pH buffers, pH adjusters, organic and inorganic salts, sugars, amino acids or surfactants may be incorporated therein. Additives which improve the solubility or pharmaceutical activity of a particular pharmaceutically active agent are preferred. More preferably, the aqueous medium is a pH controlled system including water. The pH is typically maintained at a suitable level to enhance or promote the solubility and stability of the pharmaceutically active agent. For example, in the embodiment wherein the pharmaceutically active agent is ranitidine, the pH is typically maintained between about 5.0 and about 7.5, preferably between about 5.7 to about 6.2. Methods of adjusting and maintaining a suitable pH are known to those skilled in the art. For instance, the pH may be adjusted and maintained at a suitable level using a phosphate or acetate buffer system.

The water portion into which the free base of the pharmaceutically active agent is dissolved typically comprises an inorganic acid medium. The inorganic acid medium converts the free base of the pharmaceutically active agent to a pharmaceutically acceptable salt form in situ, and therefore the pharmaceutically active agent may be considered to be present in the form of a pharmaceutically acceptable salt in solution. Examples of suitable inorganic acid medium include but are not limited to hydrochloric acid, nitric acid, and sulfuric acid. Preferably, the inorganic acid medium comprises a concentrated inorganic acid. More preferably, the inorganic acid medium comprises a concentrated solution of hydrochloric acid. Alternatively, the free base of the pharmaceutically active agent may be dissolved in an organic acid medium. Suitable organic acid media comprise concentrated solutions of citric or tartaric acid. The inorganic acid media is currently preferred for dissolving the free base of the pharmaceutically active agent.

The pharmaceutically active agent, either in salt form or as the free base, may be dissolved in the medium (either aqueous medium or inorganic acid medium) according to any suitable dissolution technique known to those skilled in the art. For example, the pharmaceutically active agent may be added to the medium and dissolved with stirring, with or without the addition of heat. Alternatively, the pharmaceutically active agent may be added to the medium and dissolved using sonication or other suitable techniques. The only requirement is that the pharmaceutically active agent be sufficiently dissolved such that no crystal formation occurs, as measured by X-ray crystallography.

The amount of pharmaceutically active agent, either in salt form or free base, which is dissolved in the water portion will be dependent upon the pharmaceutical activity and solubility of the particular agent. Generally, the amount of pharmaceutically active agent dissolved in the water portion is sufficient to deliver a therapeutically effective dose to a patient in need thereof. For example, the amount of $H_2$-antagonist typically dissolved in the water portion is between about 20 to about 80 percent by weight. Typically, the amount of pharmaceutically active agent dissolved in the water portion of the emulsion is sufficient to provide an emulsion containing between about 5 to about 60 percent of the agent.

Once the $H_2$-antagonist is dissolved in the water portion, the water portion is combined with an oil portion to form a matrix of the water portion and the oil portion (hereinafter "water portion and oil portion matrix"). As used herein, the term "matrix" refers to the combination of the water portion and the oil portion prior to emulsification. The oil portion includes an oil suitable for human consumption (i.e, an edible oil) and an emulsifying agent. Typically, suitable oils are those which are known to form water-in-oil emulsions either spontaneously or in the presence of an emulsifying agent. The oil is usually one in which the pharmaceutically acceptable salt and the free base of the pharmaceutically active agent are not soluble and which is compatible with the capsule. Suitable edible oils for use in the methods of the present invention include medium weight vegetable oils or synthetic, or semi-synthetic edible oils or combinations thereof. The term "oil" as used herein refers to a single oil or a combination of two or more oils which taken together provide the oil included in the oil portion. Vegetable oils which are useful in the present invention include soybean oil, partially hydrogenated soybean oil, corn oil, sunflower oil, peanut oil, cottonseed oil, and fractionated coconut oils.

Synthetic edible oils are useful in the present invention because of their purity and favorable physical characteristics. Suitable synthetic oils are pharmaceutically acceptable and are known to those skilled in the art. Examples of suitable synthetic oils include but are not limited to the esters and mixed esters of glycerol or propylene glycol, (hereinafter "glycerides"). The tri- or diglycerides of medium chain fatty carboxylic acids are preferred. Suitable tri- or diglycerides include $C_6$–$C_{12}$ fatty acid glycerides. Preferred triglycerides are triglycerides of $C_8$–$C_{10}$ fatty acids of fractionated coconut oil. Particularly preferred triglycerides are "Miglyols," which are triglycerides of caprylic acid and capric acid with glycerol. "Miglyols" meet the requirements of the British Pharmacopoeia 1980, Addend. 1983, for monograph "Fractionated Coconut Oil" and of the German Pharmacopoeia, DAB 8, for the monograph "Medium Chain Triglycerides".

These oils may be used as the oil itself, or as extenders of the oil portion of the emulsion. Examples of oils used as extenders of the oil portion include sugar fatty acid esters known as "Olestras" and fatty acid esters of open chain polyols, such as "Miglyols."

The oil portion of the emulsion also includes an emulsifying agent. Suitable emulsifying agents are known to those skilled in the art and include phospholipids, and anionic and nonionic surfactants or combinations thereof. The term "emulsifying agent" as used herein refers to a single emulsifying agent or a combination of two or more emulsifying agents which taken together provide the emulsifying agent included in the oil portion. The emulsifying agents useful in the present invention will be acceptable for food or pharmaceutical manufacturing purposes. In addition, suitable emulsifying agents will have a hydrophilic lipophilic balance (HLB) value of less than 6. The HLB value indicates the ability of the emulsifying agent to form and stabilize the emulsion. Examples of suitable emulsifying agents include those described in U.S. Pat. No. 3,376,199 to Coles et al., the disclosure of which is incorporated herein by reference in its entirety. More specifically, suitable emulsifying agents include:

(a) phospholipids such as soy or egg lecithin, and suitable derivatives of lechithin;

(b) polyhydric alcohols, or their anhydrides, esterified with fatty acids, such as sorbitan monooleate, sorbitan sesquioleate, sorbitan monostearate, propylene glycol monostearate, diglycol monostearate, mannitan monooleate, mannide monooleate, glycerol monostearate, propylene glycol monolaurate, diglycol monooleate, diglycol monopalmitate, diglycol monoriconoleate, pentaerythritol monostearate, pentaerythritol glycerol oleate, pentaerythritol dioleostearate, low-molecular polyoxyethylene oleate, polyglyceryl monostearate, polyglyceryol oleate, glycol monostearate, glyceryl monooleate, glyceryl monopalmitate, and low-molecular polyoxyethylene monostearate;

(c) glycerol polyhydric alcohol anhydride esters such as glycerol sorbitan laurate and glycerol mannitan laurate;

(d) polyoxyethylene fatty ethers, such as ethers having a short polyoxyethylene chain, such as polyoxyethylene (4) lauryl ether, polyoxyethylene (2) cetyl ether, polyoxyethylene (2) stearyl ether and polyoxyethylene (2) oleyl ether;

(e) solid particle emulsifying agents such as calcium oleate and magnesium stearate;

(f) anionic surfactants such as phosphotidyl compounds including those described in U.S. Pat. No. 4,788,182 to Baschang et al., the disclosure of which is incorporated herein by reference in its entirety, and (g) sulfates and sulfonates, such as sodium lauryl sulfate and dioctyl sulfosuccinate; and any suitable combination of any of the foregoing.

The preferred emulsifying agent is phosphatidyl choline. Phosphatidyl choline advantageously acts as a self emulsifier as well as part of the edible oil of the oil portion of the emulsion. According to one preferred embodiment of the present invention, the oil portion of the emulsion of the present invention comprises phosphatidyl choline extended with "Miglyol."

The water portion may be combined with the oil portion in any suitable manner. Specifically, the water portion may be added to the oil portion. Alternatively, the oil portion may be added to the water portion to provide the matrix. It is currently preferred to add the water portion to the oil portion. The oil portion is combined with the water portion in an amount sufficient to provide an emulsion which is compatible with the capsule. Typically, the oil portion is added in an amount sufficient to provide an oil portion:water portion ratio of about 6:1 to 0.5:1. Preferably, the oil portion:water portion ratio is between about 3:1 to 1:1.

The matrix is then emulsified to provide the emulsion containing the pharmaceutically active agent. Typically, the matrix is emulsified under standard conditions, which include the use of conventional stirring or mixing devices such as for example, stirrers, paddles, and homogenizers. The emulsification may take place at temperatures ranging from about 20° C. to about 80° C., preferably about 50° C. to about 60° C., for a period of time sufficient for the emulsion to become uniform and reach room temperature. Suitable time periods will of course be dependent upon the amount of water portion and oil portion to be emulsified, the particular emulsifying agent employed and the temperature at which the matrix is emulsified, and may be from about 10 seconds up to about 96 hours or longer. Preferably, the matrix is emulsified for between about 1 and about 60 minutes. The resulting emulsion is liquid or semisolid. The semisolids may have a consistency ranging from that of a lotion to that of a thick cream. Preferably, the emulsion is comprised of the water portion containing the pharmaceutically active agent as the dispersed phase and the oil portion as the continuous phase. One skilled in the art will appreciate that it is possible to prepare an emulsion wherein the water portion is the continuous phase and the oil portion is the dispersed phase. In the embodiment wherein the emulsion is filled into a capsule, emulsions wherein water is the continuous phase are not currently preferred inasmuch as the emulsion should be compatable with the capsule into which it is filled. The preferred emulsions are those wherein the water portion is sufficiently dispersed in the oil portion such that the water portion is in the form of droplets of water portion surrounded by the oil portion. Such emulsions are advantageously compatible with the capsules used in the present invention. Contrary to expectations, the water portion of the emulsion does not degrade or otherwise negatively affect the capsule.

The thus produced emulsion may then be filled into suitable capsules to provide the capsule composition of the present invention. Any suitable method of filling the capsules known to those skilled in the art may be employed. Preferably, the emulsion may be filled into the capsules using conventional, automated capsule filling techniques.

Suitable capsules include starch capsules and hard and soft gelatin capsules, which are known to those skilled in the art. Suitable soft gelatin capsules will be known to those skilled in the art and include capsules such as those described in U.S. Pat. No. 4,744,988 to Brox and U.S. Pat. No. 5,200,191 to Steele et al., the disclosures of which are incorporated herein by reference in their entirety. Suitable hard gelatin capsules for use in the method of the present invention will include hard gelatin capsules which are sealed or banded to prevent leakage of liquid contents. Examples of suitable capsules are described in U.S. Pat. No. 4,656,066 to Wittwer, the disclosure of which is incorportated herein by reference in its entirety. Currently, starch capsules, such as those described in U.S. Pat. No. 4,673,438 to Wittwer et al., the disclosure of which is incorporated herein by reference in its entirety, are preferred because of their compatibility with pharmaceutically active agents and their improved tamper resistance. The capsule should be large enough to contain a therapeutically effective dose of the pharmaceutically active agent, and small enough to be administered via the oral cavity. Accordingly, the proper capsule size will be dependent upon the pharmaceutically active agent to be administered. Size 0 or smaller capsules are preferred for the preparation of capsule compositions containing $H_2$-antagonists.

The daily dose of any particular pharmaceutically active agent may be provided in the form of one or more capsules prepared according to the present invention. The daily dose of the pharmaceutically active agent is non-toxic and therapeutically effective. Typically, the daily dose of $H_2$-antagonist is from 40 to 1600 mg, depending upon the particular $H_2$-antagonist to be administered. For example, the suggested daily dose of ranitidine and nizatidine is 150 mg, cimetidine is 300 mg, and famotidine is 20 mg. See, Histamine and Histamine antagonists, *Handbook Exp. Pharmacol.* 97:573 (1991), The capsule compositions may include a dose of from 10 to 800 mg of $H_2$-antagonist, depending on the known pharmaceutical activity and market of the $H_2$-antagonist drug. Typically, the capsule compositions are administered orally from 1 to 5 times daily.

The following examples are provided to illustrate the present invention, and should not be construed as limiting thereof. In these examples, phosphatidyl choline, medium chain glycerides, is obtained from American Lecithin Company, Danbury, Connecticut under the tradename PHOSAL 53 MCT™, propylene glycol dicaprylate/dicaprate is obtained from Dynamit Nobel, Germany under the tradename MIGLYOL 810™, size 0 starch capsules were obtained from Capsugel, Greenwood S.C., M means molar concentration, g means grams, mg means milligrams, % w/w means percent weight by weight, and °C. means degrees Centigrade.

EXAMPLE 1

Phosphate buffer (0.1M) is prepared by mixing 27.36 g of sodium phosphate dibasic, 3.0 g of potassium phosphate monobasic, and adding sufficient water to provide 6 liters.

Ranitidine hydrochloride 168 g (28% w/w) is added to 102 g (17% w/w) of 0.1M phosphate buffer.

PHOSAL 53 MCT™ (124.2 g, 20.7% w/w) and MIGLYOL 810™ (205.8 g, 34.3% w/w) are mixed. Thereafter, the oil mixture and the ranitidine solution are heated to 45° C., combined and emulsified in a Silverson emulsifier at low speed for 2 minutes. The emulsified blend is cooled to 30° C. and 600 mg is filled into size 0 starch capsules to give capsules containing 150 mg of ranitidine.

EXAMPLE 2

Xanthan gum (8 g, 2% w/w) is added to 68 g (17% w/w) of phosphate buffer pH 7.8 and stirred until dissolved. Ranitidine hydrochloride (112 g, 28% w/w) is slowly added with stirring and the solution is then heated to 55° C. ARLACEL 186™ (30 g, 7.5% w/w), Tween 80 (10 g, 2.5% w.w), and MIGLYOL 810™ (172 g, 43.0% w/w) are combined in a separate container. The mixture is heated to 55° C. The ranitidine solution is added to the oil mixture with rapid stirring, homogenized at low speed for 5 minutes, and allowed to come to room temperature with stirring. The prepared emulsion is filled into size 0 starch capsules to give 150 mg ranitidine capsules.

| Analysis of Emulsion | |
| --- | --- |
| HLB | 5.85 |
| pH | 5.74 |
| Target fill (mg) | 600 |

EXAMPLE 3

Nizatidine (15 g, 15.0% w/w) is dissolved in 15 g (15% w/w) hydrochloric acid (3N). PHOSAL 53 MCT™ (40 g, 40% w.w) is mixed with MIGLYOL 810™ (30 g, 30.0% w/w) in a separate container. The nizatidine solution is added to the oil mixture with rapid stirring, homogenized at low speed for 5 minutes, and allowed to return to room temperature with stirring. The prepared emulsion is filled into size 0 starch capsules to give a 600 mg capsule fill weight.

EXAMPLE 4

Nizatidine (17 g, 17.0% w/w) is dissolved in 17 g (17% w/w) hydrochloric acid (3N). PHOSAL 53 MCT™ (24.8 g, 24.8% w.w) is mixed with MIGLYOL 810™ (41.2 g, 41.2% w/w) in a separate container. The nizatidine solution is added to the oil mixture with rapid stirring, homogenized at low speed for 5 minutes, and allowed to return to room temperature with stirring. The prepared emulsion is filled into size 0 starch capsules to give a 600 mg capsule fill weight.

EXAMPLE 5

Cimetidine (2.6 g, 2.6% w/w) is dissolved in 17 g (17% w/w) hydrochloric acid (1N). PHOSAL 53 MCT™ (30.2 g, 30.2% w.w) is mixed with MIGLYOL 810™ (50.2 g, 50.2% w/w) in a separate container. The cimetidine solution is added to the oil mixture with rapid stirring, homogenized at low speed for 5 minutes, and allowed to return to room temperature with stirring. The prepared emulsion is filled into size 0 starch capsules to give a 600 mg capsule fill weight.

EXAMPLE 6

Cimetidine hydrochloride (1.7 g, 1.7% w/w) is dissolved in 10 g (10% w/w) water. PHOSAL 53 MCT™ (44.15 g, 44.15% w.w) is mixed with MIGLYOL 810™ (44.15 g, 44.15% w/w) in a separate container. The cimetidine solution is added to the oil mixture with rapid stirring, homogenized at low speed for 5 minutes, and allowed to return to room temperature with stirring. The prepared emulsion is filled into size 0 starch capsules to give a 600 mg capsule fill weight.

The foregoing is illustrative of the present invention and is not to be construed as limiting thereof. The invention is defined by the following claims, with equivalents of the claims to be included therein.

That which is claimed is:

1. A pharmaceutical capsule composition for the oral administration of a therapeutically effective amount of an $H_2$-antagonist, said composition comprising a capsule containing a water-in-oil emulsion having a water portion and an oil portion, said oil portion comprising an ester or mixed ester of glycerol, wherein a pharmaceutically acceptable salt of an $H_2$-antagonist is dissolved in the water portion, and said water-in-oil emulsion is compatible with said capsule.

2. The composition according to claim 1, wherein said capsule is selected from the group consisting of starch capsules, hard gelatin capsules and soft gelatin capsules.

3. The composition according to claim 1, wherein said $H_2$-antagonist is selected from the group consisting of ranitidine, cimetidine, nizatidine, famotidine, sufotidine, roxatidine, bisfentidine, tiotidine, lamtidine, niperotidine, mifentidine, zaltidine, and loxtidine.

4. The composition according to claim 1, wherein said $H_2$-antagonist is ranitidine.

5. The composition according to claim 1, wherein said oil portion of said water-in-oil emulsion comprises an edible oil and an emulsifying agent.

6. The composition according to claim 5, wherein said edible oil comprises a triglyceride of $C_8$–$C_{10}$ fatty acids of coconut oil.

7. The composition according to claim 5, wherein said edible oil comprises a triglyceride of caprylic or capric acid.

8. The composition according to claim 5, wherein said emulsifying agent is selected from the group consisting of phospholipids, anionic surfactants, and nonionic surfactants.

9. The composition according to claim 5, wherein said emulsifying agent is phosphatidyl choline.

10. The composition according to claim 1, wherein said water-in-oil emulsion has an oil portion:water portion ratio of from about 3:1 to about 1:1.

11. The composition according to claim 1, wherein the amount of $H_2$-antagonist in said water-in-oil emulsion is about 5% to 60% by weight.

12. A method of making a water-in-oil emulsion containing a pharmaceutically acceptable salt of an $H_2$-antagonist, said method comprising:

(a) dissolving said pharmaceutically acceptable salt in an aqueous medium to form a water portion;

(b) combining said water portion with an oil portion comprising an edible oil comprising an ester or mixed ester of glycerol and an emulsifying agent to form a water portion and oil portion matrix; and (c) emulsifying said matrix to form the water-in-oil emulsion.

13. The method according to claim 12, wherein said step (a) of dissolving said pharmaceutically acceptable salt in an aqueous medium comprises dissolving a pharmaceutically acceptable salt of an $H_2$-antagonist selected from the group consisting of ranitidine, cimetidine, nizatidine, famotidine, sufotidine, roxatidine, bisfentidine, tiotidine, lamtidine, niperotidine, mifentidine, zaltidine, and loxtidine in an aqueous medium.

14. The method according to claim 12, wherein said step (a) of dissolving said pharmaceutically acceptable salt in an aqueous medium comprises dissolving between about 20 and about 80 percent by weight of a pharmaceutically acceptable salt of an $H_2$-antagonist in an aqueous medium.

15. The method according to claim 12, wherein said step (b) of combining said water portion with an oil portion comprising an edible oil and an emulsifying agent comprises combining said water portion with an oil portion comprising a triglyceride of $C_8$–$C_{10}$ fatty acids of coconut oil and an emulsifying agent.

16. The method according to claim 12, wherein said step (b) of combining said water portion with an oil portion comprising an edible oil and an emulsifying agent comprises combining said water portion with an oil portion comprising a triglyceride of caprylic or capric acids and phosphatidyl choline.

17. The method according to claim 12, wherein said step (a) of dissolving said pharmaceutically acceptable salt in an aqueous medium comprises dissolving said pharmaceutically acceptable salt in 1 part water and wherein said step (b) of combining said water portion with an oil portion comprising an edible oil and an emulsifying agent comprises combining said water portion with from 3 to 1 parts by weight of a triglyceride of $C_8$–$C_{10}$ fatty acids of coconut oil and phosphatidyl choline.

18. The method according to claim 12, wherein said step (c) of emulsifying said matrix to form the water-in-oil emulsion comprises emulsifying said matrix at between about 50° C. and about 60° C. for between about 1 and about 60 minutes.

19. The method according to claim 12, wherein said step (c) of emulsifying said matrix to form the water-in-oil emulsion comprises emulsifying a water portion comprising an $H_2$-antagonist dissolved in an aqueous medium and an oil portion comprising a triglyceride of $C_8$–$C_{10}$ fatty acids of coconut oil, and phosphatidyl choline at between about 50° C. and about 60° C. for between about 1 and about 60 minutes.

20. A method of making a pharmaceutical capsule composition for the oral administration of a therapeutically effective amount of an $H_2$-antagonist, said method comprising:

(a) dissolving a pharmaceutically acceptable salt of said $H_2$-antagonist in an aqueous medium;

(b) combining said water portion with an oil portion comprising an edible oil comprising an ester or mixed ester of glycerol and an emulsifying agent, wherein said edible oil is compatible with said capsule, to form a water portion and oil portion matrix;

(c) emulsifying said matrix to form the water-in-oil emulsion; and (d) filling said capsule with said water-in-oil emulsion.

21. The method according to claim 20, wherein said step (a) of dissolving said pharmaceutically acceptable salt in an aqueous medium comprises dissolving a pharmaceutically acceptable salt of an $H_2$-antagonist selected from the group consisting of ranitidine, cimetidine, nizatidine, famotidine, sufotidine, roxatidine, bisfentidine, tiotidine, lamtidine, niperotidine, mifentidine, zaltidine, and loxtidine in an aqueous medium.

22. The method according to claim 20, wherein said step (a) of dissolving said pharmaceutically acceptable salt in an aqueous medium comprises dissolving between about 20 and about 80 percent by weight of a pharmaceutically acceptable salt of an $H_2$-antagonist in an aqueous medium.

23. The method according to claim 20, wherein said step (b) of combining said water portion with an oil portion comprising an edible oil and an emulsifying agent comprises combining said water portion with an oil portion comprising a triglyceride of $C_8$–$C_{10}$ fatty acids of coconut oil and an emulsifying agent.

24. The method according to claim 20, wherein said step (b) of combining said water portion with an oil portion comprising an edible oil and an emulsifying agent comprises combining said water portion with an oil portion comprising a triglyceride of caprylic or capric acids and phosphatidyl choline.

25. The method according to claim 20, wherein said step (a) of dissolving said pharmaceutically acceptable salt in an aqueous medium comprises dissolving said pharmaceutically acceptable salt in 1 part water and wherein said step (b) of combining said water portion with an oil portion comprising an edible oil and an emulsifying agent comprises combining said water portion with an oil portion comprising from 3 to 1 parts by weight of a triglyceride of $C_8$–$C_{10}$ fatty acids of coconut oil and phosphatidyl choline.

26. The method according to claim 20, wherein said step (c) of emulsifying said matrix to form the water-in-oil emulsion comprises emulsifying said matrix at between about 50° C. and about 60° C. for between about 1 and about 60 minutes.

27. The method according to claim 20, wherein said step (c) of emulsifying said matrix to form the water-in-oil emulsion comprises emulsifying a water portion comprising an $H_2$-antagonist dissolved in an aqueous medium and an oil portion comprising a triglyceride of $C_8$–$C_{10}$ fatty acids of coconut oil, and phosphatidyl choline at between about 50° C. and about 60° C. for between about 1 and about 60 minutes.

28. A method of making a water-in-oil emulsion containing a pharmaceutically acceptable salt of an $H_2$-antagonist, said method comprising:

(a) dissolving a free base of said $H_2$-antagonist in an inorganic acid medium to form a water portion;

(b) combining said water portion with an oil portion comprising an edible oil and an emulsifying agent to form a water portion and oil portion matrix; and (c) emulsifying said matrix to form the water-in-oil emulsion.

29. The method according to claim 28, wherein said step (a) of dissolving said free base of said $H_2$-antagonist in an inorganic acid medium comprises dissolving a free base of an $H_2$-antagonist selected from the group consisting of ranitidine, cimetidine, nizatidine, famotidine, sufotidine, roxatidine, bisfentidine, tiotidine, lamtidine, niperotidine, mifentidine, zaltidine, and loxtidine in an inorganic acid medium.

30. The method according to claim 28, wherein said step (a) of dissolving said free base of said $H_2$-antagonist in an inorganic acid medium comprises dissolving said free base of said $H_2$-antagonist in hydrochloric acid.

31. The method according to claim 28, wherein said step (a) of dissolving said free base of said $H_2$-antagonist in an inorganic acid medium comprises dissolving between about 20 and about 80 percent by weight of a free base of an $H_2$-antagonist in an inorganic acid medium.

32. The method according to claim 28, wherein said step (b) of combining said water portion with an oil portion comprising an edible oil and an emulsifying agent comprises combining said water portion with an oil portion comprising a triglyceride of $C_8$–$C_{10}$ fatty acids of coconut oil and an emulsifying agent.

33. The method according to claim 28, wherein said step (b) of combining said water portion with an oil portion comprising an edible oil and an emulsifying agent comprises combining said water portion with an oil portion comprising a triglyceride of caprylic or capric acids and phosphatidyl choline.

34. The method according to claim 28, wherein said step (a) of dissolving said free base of said $H_2$-antagonist in an inorganic acid medium comprises dissolving said free base of said $H_2$-antagonist in 1 part hydrochloric acid and wherein said step (b) of combining said water portion with an oil portion comprising an edible oil and an emulsifying agent comprises combining said water portion with from 3 to 1 parts by weight of a triglyceride of $C_8$–$C_{10}$ fatty acids of coconut oil and phosphatidyl choline.

35. The method according to claim 28, wherein said step (c) of emulsifying said matrix to form the water-in-oil emulsion comprises emulsifying said matrix at between about 50° C. and about 60° C. for between about 1 and about 60 minutes.

36. The method according to claim 28, wherein said step (c) of emulsifying said matrix to form the water-in-oil emulsion comprises emulsifying a water portion comprising a free base of an $H_2$-antagonist dissolved in an inorganic acid medium and an oil portion comprising a triglyceride of $C_8$–$C_{10}$ fatty acids of coconut oil, and phosphatidyl choline at between about 50° C. and about 60° C. for between about 1 and about 60 minutes.

37. A method of making a pharmaceutical capsule composition for the oral administration of a therapeutically effective amount of an $H_2$-antagonist, said method comprising:

(a) dissolving a free base of said $H_2$-antagonist in an inorganic acid medium;

(b) combining said water portion with an oil portion comprising an edible oil and an emulsifying agent, wherein said edible oil is compatible with said capsule, to form a water portion and oil portion matrix;

(c) emulsifying said matrix to form the water-in-oil emulsion; and (d) filling said capsule with said water-in-oil emulsion.

38. The method according to claim 37, wherein said step (a) of dissolving said free base of said $H_2$-antagonist in an inorganic acid medium comprises dissolving said free base of an $H_2$-antagonist selected from the group consisting of ranitidine, cimetidine, nizatidine, famotidine, sufotidine, roxatidine, bisfentidine, tiotidine, lamtidine, niperotidine, mifentidine, zaltidine, and loxtidine in an inorganic acid medium.

39. The method according to claim 37, wherein said step (a) of dissolving said free base of said $H_2$-antagonist in an inorganic acid medium comprises dissolving said free base of said $H_2$-antagonist in hydrochloric acid.

40. The method according to claim 37, wherein said step (b) of combining said water portion with an oil portion comprising an edible oil and an emulsifying agent comprises combining said water portion with an oil portion comprising a triglyceride of $C_8$–$C_{10}$ fatty acids of coconut oil and an emulsifying agent.

41. The method according to claim 37, wherein said step (b) of combining said water portion with an oil portion comprising an edible oil and an emulsifying agent comprises combining said water portion with an oil portion comprising a triglyceride of caprylic or capric acids and phosphatidyl choline.

42. The method according to claim 37, wherein said step (a) of dissolving said free base of said $H_2$-antagonist in an inorganic acid medium comprises dissolving said free base of said $H_2$-antagonist in 1 part hydrochloric acid and wherein said step (b) of combining said water portion with an oil portion comprising an edible oil and an emulsifying agent comprises combining said water portion with an oil portion comprising from 3 to 1 parts by weight of a triglyceride of $C_8$–$C_{10}$ fatty acids of coconut oil and phosphatidyl choline.

43. The method according to claim 37, wherein said step (c) of emulsifying said matrix to form the water-in-oil emulsion comprises emulsifying said matrix at between about 50° C. and about 60° C. for between about 1 and about 60 minutes.

44. The method according to claim 37, wherein said step (c) of emulsifying said matrix to form the water-in-oil emulsion comprises emulsifying a water portion comprising an $H_2$-antagonist dissolved in an inorganic acid medium and an oil portion comprising a triglyceride of $C_8$–$C_{10}$ fatty acids of coconut oil, and phosphatidyl choline at between about 50° C. and about 60° C. for between about 1 and about 60 minutes.

45. A pharmaceutical capsule composition for the oral administration of a therapeutically effective amount of an $H_2$-antagonist, said composition comprising a capsule containing a water-in-oil emulsion having a water portion and an oil portion, wherein a pharmaceutically acceptable salt of an $H_2$-antagonist is dissolved in the water portion, wherein said water-in-oil emulsion is compatible with said capsule, and wherein said water-in-oil emulsion comprises an edible oil comprising a triglyceride of $C_8$–$C_{10}$ fatty acids of coconut oil or a triglyceride of caprylic or capric acid.

46. A method of making a water-in-oil emulsion containing a pharmaceutically acceptable salt of an $H_2$-antagonist, said method comprising:

(a) dissolving said pharmaceutically acceptable salt in an aqueous medium to form a water portion;

(b) combining said water portion with an oil portion comprising an edible oil and an emulsifying agent to form a water portion and oil portion matrix, wherein said edible oil is a triglyceride of $C_8$–$C_{10}$ fatty acids of coconut oil or a triglyceride of caprylic or capric acids; and (c) emulsifying said matrix to form the water-in-oil emulsion.

47. A method of making a pharmaceutical capsule composition for the oral administration of a therapeutically effective amount of an $H_2$-antagonist, said method comprising:

(a) dissolving said pharmaceutically acceptable salt of said $H_2$-antagonist in an aqueous medium;

(b) combining said water portion with an oil portion comprising an edible oil and an emulsifying agent, wherein said edible oil is compatible with said capsule, to form a water portion and oil portion matrix, and wherein said edible oil comprises a triglyceride of $C_8$–$C_{10}$ fatty acids of coconut oil or a triglyceride of caprylic or capric acids;

(c) emulsifying said matrix to form the water-in-oil emulsion; and (d) filling said capsule with said water-in-oil emulsion.

\* \* \* \* \*